United States Patent [19]
Kitamori et al.

[11] Patent Number: 5,178,836
[45] Date of Patent: Jan. 12, 1993

[54] ANALYTICAL METHOD FOR PARTICULATE SUBSTANCES, RELEVANT ANALYTICAL EQUIPMENT AND ITS APPLICATION SYSTEM

[75] Inventors: Takehiko Kitamori; Kenji Yokose; Tetsuya Matsui, all of Hitachi; Masaharu Sakagami, Katsuta, all of Japan

[73] Assignee: Hitachi, Ltd., Tokyo, Japan

[21] Appl. No.: 334,358

[22] Filed: Apr. 7, 1989

[30] Foreign Application Priority Data

Apr. 8, 1988 [JP] Japan ................................. 63-85094

[51] Int. Cl.⁵ ............................................. G01N 21/00
[52] U.S. Cl. ............................ 422/73; 356/335; 356/336; 356/318; 356/432; 73/24.03; 73/28.01; 73/865.5; 73/601; 73/643; 73/61.71
[58] Field of Search ............... 73/24.03, 28.01, 61 R, 73/865.5, 601, 643; 356/335, 336, 318, 432 T; 422/73

[56] References Cited

U.S. PATENT DOCUMENTS

| | | | |
|---|---|---|---|
| 3,901,599 | 8/1975 | Meric | 356/318 |
| 4,191,475 | 4/1980 | Sourrouille | 356/318 |
| 4,497,208 | 2/1985 | Oja et al. | 73/61 R X |
| 4,557,137 | 12/1985 | Kitamori et al. | 73/53 |
| 4,561,777 | 12/1985 | Radziemski et al. | 356/318 |
| 4,632,561 | 12/1986 | Rosenowaig et al. | 356/432 T |
| 4,690,558 | 9/1987 | Tsunoyama et al. | 356/318 |
| 4,722,602 | 2/1988 | Kitamori et al. | 356/336 |
| 4,738,536 | 4/1988 | Kitamori et al. | 73/657 X |
| 4,808,828 | 2/1989 | Kitamori et al. | 250/458.1 |
| 4,887,600 | 12/1989 | Watson et al. | 606/128 |
| 4,890,925 | 1/1990 | Kitamori et al. | 356/442 X |
| 4,925,307 | 5/1990 | Cremers et al. | 356/318 |
| 4,932,954 | 7/1990 | Wondrazek et al. | 606/15 X |
| 4,959,301 | 9/1990 | Weaver et al. | 435/6 X |

FOREIGN PATENT DOCUMENTS 61-229741  6/1987  Japan ................................. 356/318

Primary Examiner—Robert J. Warden
Assistant Examiner—Stephanie Blythe
Attorney, Agent, or Firm—Antonelli, Terry, Stout & Kraus

[57] ABSTRACT

This invention relates to an analytical method and a relevant equipment for particulate substances in a sample with the detection of acoustic waves generated in the sample with the irradiation of onto the sample. In this invention, the light power density of the irradiating light onto the sample is set high enough above the breakdown threshold of the particulate substances in the sample, and low enough below the breakdown threshold of the media, and the particulate substances in the sample are counted by detecting the acoustic waves generated by the breakdown of the particulate substances. The particulate substances are also analyzed for their components on the basis of the light signal (emission spectrum) which is detected with a dispersed spectrum from the light which is generated by the breakdown of the particulate substances.

25 Claims, 5 Drawing Sheets

ANALYTICAL METHOD FOR PARTICULATE SUBSTANCES, RELEVANT ANALYTICAL EQUIPMENT AND ITS APPLICATION SYSTEM

BACKGROUND OF THE INVENTION

This invention relates to an analytical method for particulate substances and relevant analytical equipment, as well as to its application system, and especially relates to the analytical method and the relevant analytical equipment as well as to its application system which is advantageous for exclusively analyzing particulate substances contained in liquid or gas (for instance, determining the particle-count of particulate substances contained in the liquid, while not erroneously counting air bubbles.)

An existing analytical method is described in the laid-open patent application: SHO 62-38345 relating to an analytical method for particulate substances in liquids using photoacoustic spectroscopy. This conventional photoacoustic spectroscopy works in such a way that the particulate substances contained in a fluid sample are irradiated with light to generate heat energy with provisions arranged to prevent the generation of acoustic waves, and the heat energy generated converts into acoustic waves which are continuously detected to represent the particle-count in a fluid sample. It has been revealed by the work of the inventors, though the cited literature did not state such clearly, that the acoustic waves generated at a high irradiation intensity were those caused by optical breakdown.

This invention relates to a method of detecting particulate substances on the basis of the optical breakdown of particles, and according to the inventors' work, it is a new finding whereby the threshold value for the optical breakdown of the particles is smaller than the threshold value for the optical breakdown of liquid or air, details of which are given herein.

However, this fact was not perceived in the conventional analytical method, and the irradiating light intensity or the power density was not set at a high enough value above the threshold value of the breakdown in comparison with the particles or low enough below the threshold value of the breakdown in comparison with the media or air bubbles. That is to say, in the conventional analytical method, the power density of irradiating light was sometimes one that generates no acoustic waves breakdown the particles, or sometimes one which induces breakdown not only of particle but also of media or air bubbles. Therefore, the aforementioned conventional technology cannot induce the selective breakdown of particles. Accordingly, the reliability of the measured results was low because miscounts for air bubbles or the like were included.

Furthermore, there is a description in the laid-open patent application: SHO 62-38345, that the method offers the possibility of analyzing the components of the particle on the basis of the dependency of the signal magnitude upon wave length, using a variable wave length-type high-power laser unit. However, the component analysis of the particle described was impossible because of the difficulty of obtaining particular signals representing the proper characters of the components consisting of individual particles, for the reason that the conventional technology was a component analysis based on the absorption spectrum of the whole sample existing in the irradiated area.

SUMMARY OF THE INVENTION

The object of the invention is to offer an analytical method and relevant equipment for particulate substances which can perform selective analysis (especially for particle-count) for particulate substances from media or air bubbles.

In addition, the object of the invention is also to offer an analytical method and the relevant equipment which can perform component analysis of particulate substances.

In addition, the object of the invention is also to build a control system for an ultrapure water supplier using the equipment which analyzes (particle-count and component analysis) particulate substances selectively from media or air bubbles.

The above-mentioned objects will be achieved by measuring the acoustic waves or the light emission from the selective breakdown of particles contained in the media.

That is to say, the analytical method of the invention is a method by which particulate substances are be analyzed by detecting acoustic waves generated in the sample which is irradiated with light. And the power density of the irradiating light onto the sample is set high enough above the threshold value to breakdown the particulate substances in the sample, and low enough below the breakdown threshold of the media. And the acoustic waves thus generated are detected and analyzed (especially for particle-count) for the particulate substance in the sample. In addition, with this method, the particle size of the particulate substances can be measured using the pulse height of the detected acoustic waves.

In addition, another analytical method of the invention analyzes the particulate substances (especially for component analysis on the basis of emission spectrums) with the signal detected in the spectrum of the light generated from the breakdown of the particulate substances, by setting the power density of the light irradiating onto the sample high enough above the threshold value for the breakdown of the particulate substances in the sample, and low enough below the threshold value for the breakdown of the media. In this analytical method for particulate substances on the basis of the light signal, it is effective to use light irradiating onto the sample having a wave length apart from the wave length range for the emission spectrum to be measured.

In addition, another analytical method of the invention combines the aforementioned analytical method for the particulate substances based on the detection of acoustic waves with the above-mentioned analytical method for particulate substances based on the detection of light signals, and uses it to detect and count particles of particulate substances in the sample on the basis of detected acoustic waves. It then makes a component analysis of the particulate substances on the basis of the emission spectrum detected by the light which is dispersed into a spectrum.

In this analytical method, when the sample is in the liquid phase, it is advisable to keep the power density of the irradiating light low enough below the threshold value for the breakdown of the gas.

The analytical equipment of the invention consists of an irradiation device which irradiates light having a power density set high enough above the threshold value to breakdown the particulate substances in a sample and low enough below the threshold value for the breakdown of the media; an acoustic wave detector which detects the acoustic waves generated in the sample; and a signal processing device which identifies particular acoustic waves generated by the breakdown of the particulate substances from the outgoing signals from the above-mentioned acoustic wave detector and to detect and count particles for the particulate substances in the sample. In this analytical equipment, the above-mentioned signal processing device should have a computing function for particle size on the basis of the pulse height of the detected acoustic waves.

Another analytical equipment of the invention consists of an irradiation device which irradiates light with the power density set high enough above the threshold value to breakdown the particulate substances in a sample and low enough below the threshold value for the breakdown of the media; a spectroscope which disperses light generated in the sample into a spectrum; a photo-detector which detects light coming from the spectrometer; and a signal processing device which analyzes (especially component analysis for the particulate substances) particulate substances on the basis of the signal (emission spectrum) from the photo-detector. In this analytical equipment, it is desirable to use light irradiating from the above-mentioned device onto the sample with a wave length that is outside the wave length range of the emission spectrum to be measured.

Another analytical equipment of the invention consists of an irradiation device which irradiates light with an power density set high enough above the breakdown threshold of the particulate substances in a sample, and low enough below the breakdown threshold of the media; an acoustic wave detection device which detects the acoustic wave generated by the breakdown in the sample; a photo-detection device which disperses the light coming from the sample into a spectrum and detects it; and a signal processing device which identifies the particulate substances in the sample on the basis of the acoustic wave signal detected by the acoustic wave detection device, and for the component analysis of the particulate substances on the basis of the light signal (emission spectrum) detected by the photo-detection device.

In addition, in the above-mentioned analytical equipment, it is desirable that the irradiation device have an adjusting means which allows the light power density of the irradiating light from the device to be set high enough above the breakdown threshold of the particulate substances and low enough below the breakdown threshold of the media.

In addition, in the aforementioned analytical methods and equipment, it is desirable that the irradiating light be generated by pulses oscillation.

In addition, if filtered serum is used as a sample, viruses can be analyzed as particulate substances with these analytical methods and equipment.

In addition, in these analytical methods and equipment, a threshold value for breakdown the particulate substances is defined on the basis of the power density of the irradiating light; however, it can also be defined on the basis of the electric field strength which is generated in a sample. That is to say, in the aforementioned analytical methods, an electric field maybe built in the sample to form an electric field strength which is high enough above the breakdown threshold of particulate substances and low enough below the breakdown threshold of media.

An ultrapure water supplier control system of the invention uses analytical equipment to analyze particulate substances on the basis of the aforementioned light signal. Part of the ultrapure water produced in the ultrapure water supplier, which consists of two or more components, is introduced into the analytical equipment as a sample. A component which may cause a defect if produced in ultrapure water is detected on the basis of component analysis performed by the analytical equipment. The control system sends back the ultrapure water produced when the defective results were detected to the defective component. In the system, it is desirable that the component to which the produced ultrapure water is sent back be another component, which is running normally, of the same kind as the defective one.

Another ultrapure water supplier control system of the invention uses analytical equipment which detects and counts particles of particulate substances on the basis of the aforementioned acoustic waves. The ultrapure water supplier consists of two or more components, and at least part of the ultrapure water produced by it is introduced into the analytical equipment as a liquid sample. In the event that a higher particle-count than that specified is detected in the produced ultrapure water, the control system stops the supply from the ultrapure water supplier to use-points, and simultaneously sends back the ultrapure water produced to the equipment located at the upper side of the ultrapure water supplier.

BRIEF DESCRIPTION OF THE DRAWINGS

FIG. 6 (a), and (b) show a sectional view of a cell for simultaneously measuring breakdown acoustic wave and light emission: FIG. 6 (a) shows a sectional view; FIG. 6 (b) shows a side view.

DETAILED DESCRIPTION OF THE PREFERRED EMBODIMENT

Figure 1:
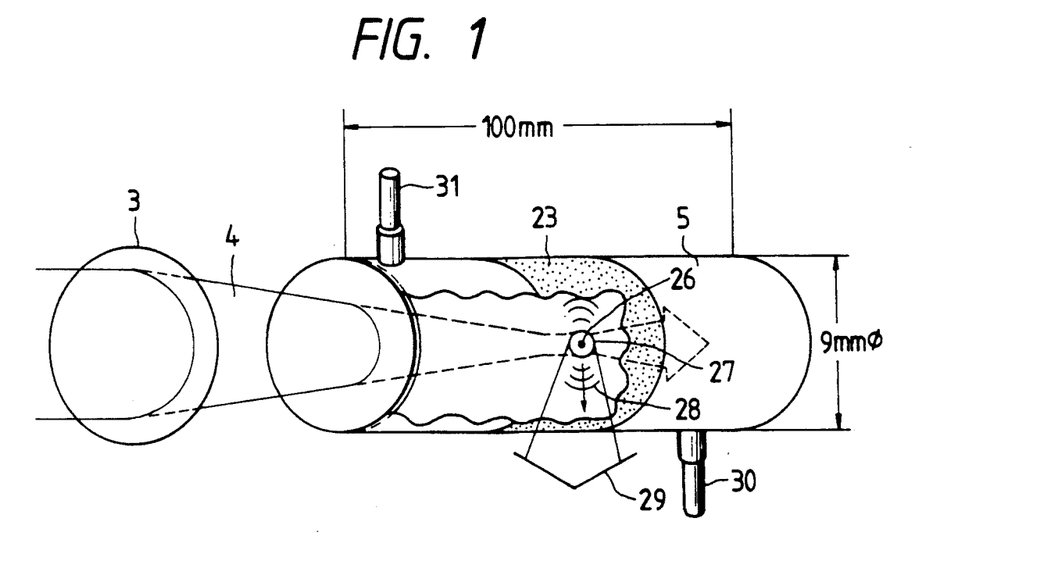
FIG. 1 shows the cell construction and particle counting principle of the invention.
Figure 5:
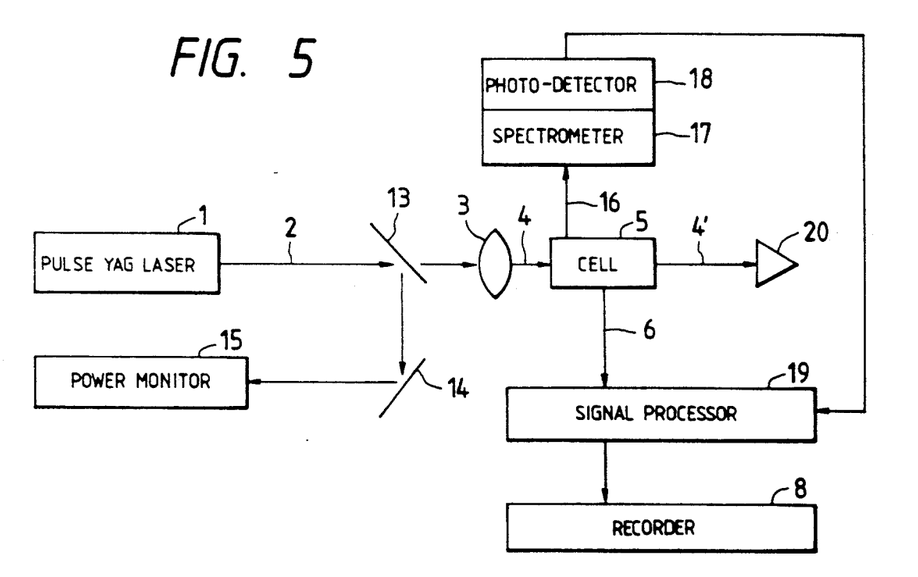
FIG. 5 shows a construction diagram of an embodiment of the invention for counting particles and analyzing components.

First, the principle of the invention is explained. FIG. 1 shows the principle of the analytical method of the invention. A liquid sample is used. The liquid sample is taken into a cell, 5. The sample is introduced from an entrance, 30, and is drained from an exit, 31. An optical window is provided at an end of the cell. The light condensed with a lens, 3 (excited light), 4 irradiates the liquid sample through the optical window. When the electric field strength generated by the light in the sample is set at a level higher that is than the breakdown threshold of the particle, 26, the particle turns into plasma (27), accompanied by a powerful acoustic wave, 28, or light emission, 29. This invention relates to the analysis of particles using the acoustic wave which is detected by a piezoelectric element, 23, as shown in FIG. 5, for instance, or using the light emission which is detected by a spectrometer and a photo-detector through the optical window formed in the shell of the cell as shown in FIG. 6, for instance.

Now, Table 1 shows breakdown threshold for a particle (polystyrene particle), water and air obtained in experiments conducted by the inventor.

TABLE 1

| Substance | Compared breakdown threshold (unit: W/cm$^2$) | |
|---|---|---|
| | Our experiments | Literature* |
| Gas (air) | $\sim 10^{12}$ (5 $\times$ 10$^{12}$) | $10^7 \sim 10^8$ |
| Liquid (water) | $10^{12} \sim 10^{11}$ (3 $\times$ 10$^{11}$) | $10^{10} \sim 10^{11}$ |
| Particle (polystyrene) | $\sim 10^{10}$ (4 $\times$ 10$^{10}$) | |

*Appl. Spectrosc. 38, p. 721 (1984)

According to the experimental results by the inventors, the breakdown threshold of the particle is lower than that of a gas such as air and a liquid such as water, unlike experimental results reported in Appl. Spectrosc. 38, 721 (1984). Therefore, by utilizing these newly obtained experimental results, and by setting light intensity or power density high enough above the breakdown threshold of particles and low enough below the breakdown threshold of gas or liquid, selective breakdown of particles can be achieved without breakdown gas or liquid. As a result, the detection of acoustic waves or light emission from the breakdown is nothing but the detection of acoustic waves or light emission generated only from particles which enables this method to analyze particulate substances in a way that is fundamentally free from miscounts caused by the breakdown of air bubbles or media. With this invention, because the media does not breakdown, there exists no background in principle, and even very fine particles of 0.1 um or smaller, a so-called ultrafine particle, can be detected and counted.

For the analysis of the particulate substances, a particle-count is obtained by counting acoustic waves. Because the pulse height of the broken-down acoustic wave depends upon particle size, the particle size can be measured from the pulse height of the broken-down acoustic wave and the information on particle size distribution is obtained from the pulse height distribution.

Thanks to the emission caused by plasma generated by breakdown, a particle-count is obtained by detecting the plasma emission when analyzing particulate substances. In this case, discrimination from the irradiating excited light or the dispersed excited light due to air bubbles can be achieved by photo-detection through a spectrometer (observing emission spectrum.) Furthermore, there are substances which consist of particles existing as ions having various ionic charges in the plasma generated by breakdown, and they are excited or inhibited by photo-energy or heat energy. Accordingly, by detecting the light emission from the plasma dispersing in a spectrometer, an emission spectrum from the ions, as well as from the neutral atoms generated by the rebounding of ions with electrons, can be obtained. The components of the particle can be analyzed (identified) from the emission spectrum, and the concentration of the components can be obtained from the corresponding emission intensity. In addition, easier measurement is realized utilizing a wave length for irradiation that is different from the wave length range of the emission spectrum.

The analysis of the particulate substances on the basis of acoustic waves and the analysis of the particulate substances on the basis of photo-emission are performed either independently or in combination. The breakdown threshold of the particles was explained using the power density of the light (W/cm$^2$), since the breakdown was caused by irradiation; however, it can also be specified with electric field strength (V/cm), because breakdown occurs when the electric field strength formed in the sample exceeds the breakdown threshold of the particles. In this case, to achieve the selective breakdown only of the particles, it can be said to be advantageous that the electric field strength is so formed in the sample as to be high enough above the breakdown threshold of the particulate substances in the sample and low enough below the breakdown threshold of the media.

Applying the analytical method of the invention for the particulate substances to the ultrapure water supplier control system, the method allows the system to detect ultrafine particles, and it can supply ultrapure water to the use-points (semiconductor fabrication unit, for instance,) with high reliability. Furthermore, since the analytical method of the invention for particulate substances also offers component analysis for the particles, defective equipment can be found among the components which compose the ultrapure water supplier, and by sending back the ultrapure water produced to the defective equipment, the operating efficiency of the system is improved.

It is considered that the discrepancy between our experimental results and the data from the cited literature is due to the following reasons. In our experiments, we used a clean space and sample when we made measurements of the threshold values at which gas or liquid breakdown. The analytical method described in the cited literature detects the dissolved (ionic) components by forcibly breaking them down in a liquid stage; however, no experimental conditions were found relating to the explicit utilization of a clean space or sample when measuring the threshold values for breakdown gas or liquid. Accordingly, for the experimental conditions in the literature, we think apparent lower threshold values were observed because breakdown was induced not for pure gas or liquid but was partly accompanied by the breakdown of impurities.

Next, we explain about the embodiment of the invention referring to FIGS. 2 through 7.

Figure 2:
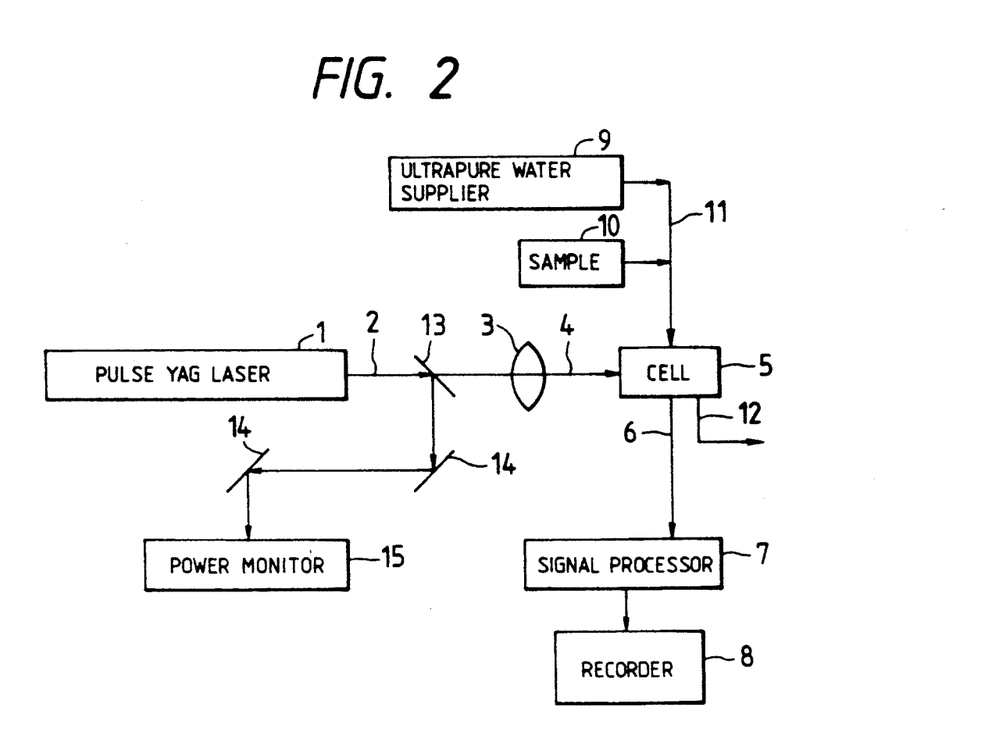
FIG. 2 shows a construction diagram of an embodiment of the invention for counting particles.

FIG. 2 shows a construction diagram for the embodiment of the case for counting the ultrafine particles in a liquid by detecting only the acoustic wave generated by the breakdown. Using a pulse YAG laser 1 as the light source, the second harmonic, 2, of wavelength 532 nm from the light source is condensed to generate excited light, 4, with a lens, 3, and is projected onto a cell, 5. The second harmonic, 2, coming from the YAG laser 1 is introduced to a optical power monitor, 15, through a half mirror, 13, and a mirror, 14, and the intensity of the light coming from the YAG laser 1 is monitored. The pulse length of the excited light, 4, is set to 10 ns and the intensity is set to 27.5 mJ, and the focal length of the condenser, 3, is 200 mm. A pulse-generated light source is utilized because it makes it easier to obtain light with a high power density. The construction of the cell, 5, is the same as that shown in FIG. 1, which has an inside diameter of 9 mm and a length of 100 mm. The breakdown acoustic signal generated in the cell is converted into an electric signal, 6, in a piezoelectric element, 23, shown in FIG. 1, and is fed to a signal processor, 7. In the signal processor, each broken-down acoustic signal is counted and measured for its pulse height, then the pulse height distribution is sent to a recorder, 8. A sample flows into the cell, 5, through a sample line, 11, and flows out as drainage 12. The sample line, 11, is directly joined with an ultrapure water supplier, 9, and an introducing device for calibrating the standard sample, 10. From the optical arrangement of the equipment and the parameters of the excited light, the power density at the position near the focus of the laser light reaches $5 \times 10^{10}$ W/cm$^2$, and the power density of the excited light exceeds the breakdown threshold of the particles, and is lower than the breakdown threshold of liquid or gas, thus the excited light can induce the breakdown of the particles only.

Figure 3:
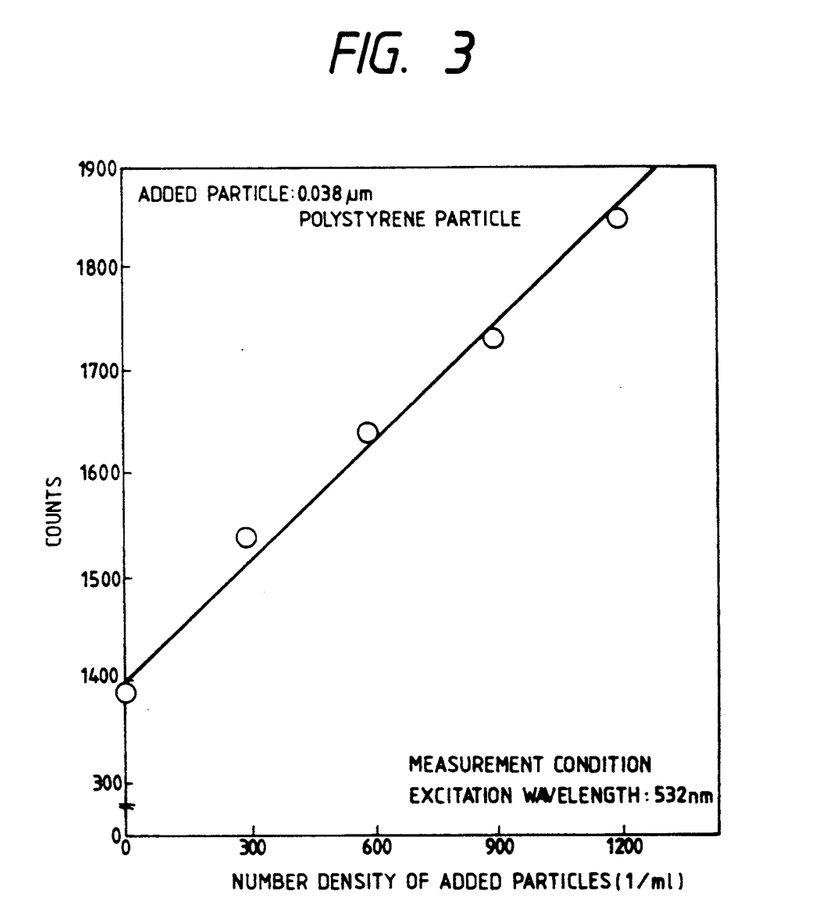
FIG. 3 shows a regression line for polystyrene particles.

FIG. 3 shows the particle-count for polystyrene standard particles of 0.038 μm. The sample was prepared in such a way that polystyrene ultrafine particles were admixed with ultrapure water to form a density of 1200 ml$^{-1}$. As seen in FIG. 3, the particle-count increased in proportion to the increasing density of particles added, and we verified that the invention offered a means to count the number of ultrafine particles in the liquid. Furthermore, the measured result shown in FIG. 3 represents the calibration curve for the present embodiment of the invention. In addition, we did not give a positive deaeration in this experiment. Though the particle count for ultrafine particles obtained by conventional laser dispersion was unreliable because of miscounts due to air bubbles, we could obtain a good calibration curve free from miscounts due to air bubbles in this embodiment of the invention.

Figure 4:
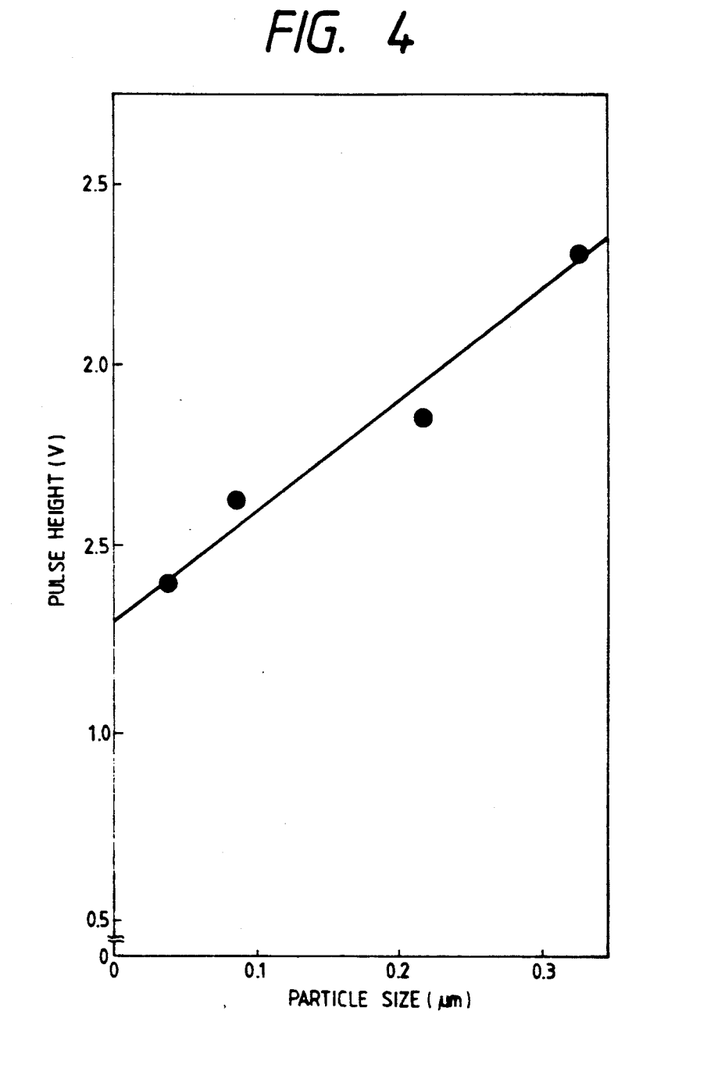
FIG. 4 shows the dependent relation between pulse height and particle size.

In this embodiment of the invention, we measured the particle size dependency of the pulse height of the acoustic signals by breakdown. FIG. 4 shows the results. The pulse height increases as particle size increases, and we verified that the particle size can be measured using the invention. FIG. 4 shows the calibration curve for particle size measurement using this embodiment of the invention.

Figures 6A, 6B:
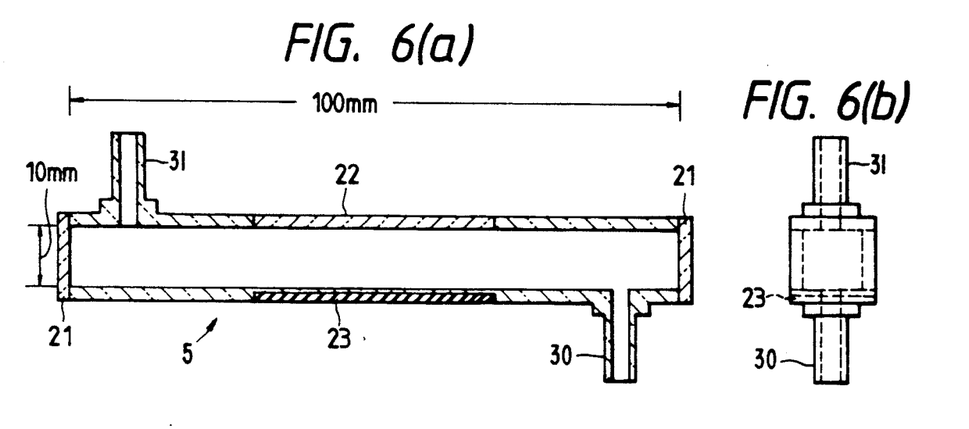

Secondly, in FIG. 5, we show an embodiment of the invention in which particles are counted and their components are analyzed. The light source and optical system employed are the same as those employed in the previous embodiment of the invention. As can be seen in FIGS. 6(a) and 6(b), we used a cell, 5, having a construction which allows the simultaneous measurement of photo-emission and acoustic waves. That is to say, excited light, 4, is projected onto one of the optical windows for incoming exciting light, 21, and induces the breakdown of particles around the center of the cell, 5. The acoustic waves generated by breakdown are detected with a piezoelectric element, 23, while the light proceeds by photo-emission to a spectrometer, 17, shown in FIG. 5 through an optical window, 22. The light penetrating 4' through the cell, 5, is terminated with a beam stopper, 20. The light that proceeds to the spectrometer, 17, gives a spectrum which is detected by a photo-detector as an emission spectrum. The emission spectrum and the acoustic signal are treated in a signal processor, 19, which sends the pulse height and the particle count of the acoustic signal, the peak wavelength and peak height of the photo-emission to a recorder, 8, and the recorder analyzes these data to print out data for particle size and component materials.

The method of making a particle count and measuring particle size is the same as those used in the previous embodiment of the invention. We analyzed particulate impurities contained in ultrapure water by taking a sample of ultrapure water.

We obtained the following information from the recorder:
Count of the acoustic waves: 1560 counts
Pulse height of the acoustic waves: 1.45 V
Emission spectrum (peak wave length): 256 nm, 777 nm The calibration curve shown in FIG. 3 tells us that if 40 counts correspond to a density of 100 ml$^{-1}$, then the acoustic wave count of 1560 corresponds to a density of 4400 ml$^{-1}$. Referring to FIG. 4, the pulse height 1.45 V corresponds to particle size 0.05 μm. Furthermore, the peak wavelength of the emission spectrum 256 nm and 777 nm coincide with photo-emission of Si and O, respectively. Accordingly, the elements composing this particulate substance are Si and O, which means they are identified as silica. From the above, we can find that the analytical results of the particulate substances in ultrapure water taken as the sample indicates silica, having a particle size 0.05 μm, and a density of 4400 ml$^{-1}$.

We verified that particle size, density and components or materials of the particulate substances can be analyzed with the above embodiment of the invention. Furthermore, together with the results of the previous embodiments of the invention, we confirmed that the ultrafine particles in the liquid can be counted without errors due to air bubbles and their components can be analyzed using the invention.

In addition, the well known conventional laser dispersion method employs the principle whereby a sample is irradiated with a laser, and the particulate substances are detected with light dispersed by particles. However, in this conventional laser dispersion method, the light dispersed by media forms a background which disturbs the measurement of light dispersed by particles, and as a result, ultrafine particles (0.1 μm or smaller) could not be counted with the conventional method. With the analytical method of the invention, ultrafine particles (0.1 μm or smaller) can be counted with sufficient accuracy.

The above-mentioned analytical method and equipment can be applied to an analytical method for viruses. That is to say, when filtered serum is taken as a material in the invention, a virus in the serum can be analyzed and identified. Normally, a virus is a giant protein having a particle size 0.1 μm or smaller, therefore, when serum is filtered with a filter of 0.1 μm, a virus passes through the filter and goes into the filtrate. When the filtrate is analyzed with the analytical equipment shown in the embodiment No. 2 of the invention, the components of the virus can be analyzed using the breakdown of the virus. Species of the virus can be identified from the results of component analysis, and the number density of the virus can be determined from the acoustic wave count for breakdown. The density can also be determined from the count of observed emission spectrum.

Figure 7:
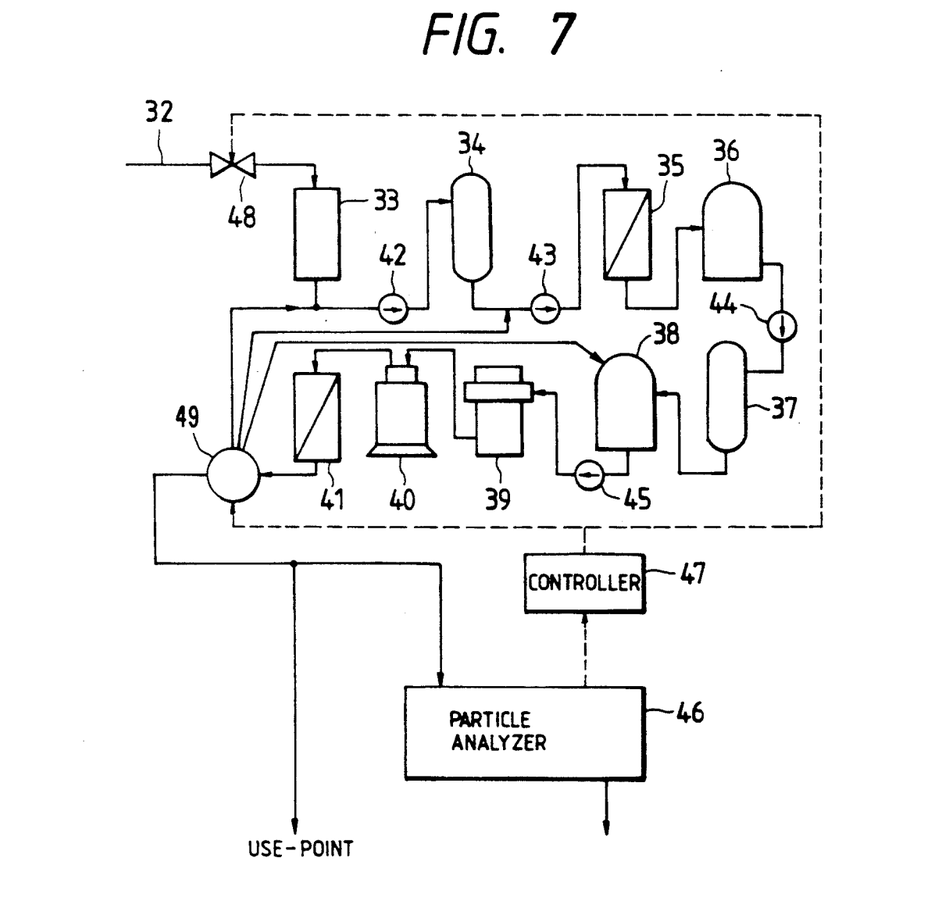
FIG. 7 shows a system diagram for applying the invention to an ultrapure water supplier.

FIG. 7 shows an ultrapure water supply system, where the analytical equipment of the invention is applied to an ultrapure water supplier.

Referring to the figure, 32 represents a feed water supply line which supplies feed water such as tap water to a distillation column, 33 and 34 represent an activated carbon filter which removes organic matter, etc., 35 represents a reverse osmosis membrane module which removes particles, electrolytes, etc., 36 represents an intermediate tank, 37 represents an ion-exchange resin which removes electrolytes, etc., 38 represents a pure water tank which stores produced pure water (specific electric resistance 1~10 MΩcm or higher), 39 represents an ultraviolet sterilizer which sterilizes bacilli, 40 represents a polisher which removes electrolytes, 41 represents an ultrafiltration membrane module which removes fine particles etc., and from this ultrafiltration membrane module, 41, to a five-way valve, 49, ultrapure water of the quality level around specific electric resistance 18~MΩcm or higher, particles having particle size 0.05~0.1 μm or larger 50 cc or less, live bacilli 0.1 cc, is supplied. In the figure, 42 through 45 represent a water feed pump or a pressurizing pump.

The ultrapure water produced is delivered from the five-way valve, 49, to an impurity analyzer (analytical equipment for particulate substances), 46. The results analyzed at the impurity analyzer, 46, are sent to a controller, 47, and the controller, 47, transmits signals to control a valve, 48, which is located in the feed water supply line and the five-way valve, 49, respectively, in accordance with the analyzed results. That is to say, the controller, 47, identifies the component equipment which may become a cause of defective ultrapure water using the results of a component analysis from the analyzer, and takes the step of sending back the ultrapure water produced to the equipment causing the defect when defective ultrapure water is detected. For example, defective ultrapure water is to be sent back either to the activated carbon filter, 34, the reverse osmosis membrane module, 35, or the ultraviolet sterilizer, 39. In this system, when two or more lines of ultrapure water supplier are in service, it is desirable that defective ultrapure water is sent back to the equipment, which is running normally, and is of the same kind as the one which is defective.

There is another way of constructing an ultrapure water supplier control system based on a count of particulate substances. That is to say, using analytical equipment which detects and counts particles on the basis of acoustic waves, and with ultrapure water introduced into the analytical equipment as a sample. The system is constructed so as to stop the ultrapure water supply from the ultrapure after supplier at use-points, and to send back ultrapure water produced to the equipment which is located upstream of the ultrapure water supplier, when higher particulate substances contained in the ultrapure water than those specified are counted.

We claim:

1. A method for enabling fluid sample analysis including analysis of a particulate substance within a fluid sample, comprising the steps of:
   applying energy to a fluid sample sufficient to cause breakdown of a particulate substance contained within the fluid sample so as to generate a signal indicative of the particulate substance as a result of the breakdown of the particulate substance, applied energy being insufficient to cause a breakdown of the fluid sample;
   detecting the generated signal resulting from the breakdown of the particulate substance; and
   analyzing the detected signal so as to obtain information relating to the particulate substance.

2. A method accoding to claim 1, wherein the energy is applied to the fluid sample so as to only cause an optical breakdown of the particulate substance.

3. A method according to claim 1, wherein the step of applying energy includes irradiating the fluid sample with light having a power density above a breakdown threshold value of the particulate substance and below a breakdown threshold value of the fluid sample.

4. A method according to claim 3, wherein the step of detecting includes detecting an acoustic wave signal resulting from breakdown of the particulate substance.

5. A method according to claim 4, wherein the step of analyzing includes determining a number of the particulate substance by counting a number of generated acoustic wave signals detected.

6. A method according to claim 4, wherein the step of analyzing includes measuring a particle size of the particulate substance in accordance with a pulse height of the detected acoustic wave signal.

7. A method according to claim 4, wherein the step of applying irradiating light includes applying pulse oscillation light.

8. A method according to claim 4, wherein the fluid is a liquid and the power density of the irradiating light is also below a breakdown threshold value of gas contained in the liquid.

9. A method according to claim 3, wherein the fluid sample is a filtered serum and the particulate substance includes at least one virus.

10. A method according to claim 4, wherein the step of detecting further includes detecting an emission light signal resulting from breakdown of the particulate substance.

11. A method according to claim 3, wherein the step of detecting includes detecting an emission light signal resulting from breakdown of the particulate substance.

12. A method according to claim 11, wherein the step of applying irradiating light includes applying a pulse oscillation light.

13. A method according to claim 11, wherein the fluid sample is a liquid and the power density of the irradiating light is also below a breakdown threshold value of a gas contained in the liquid.

14. A method according to claim 11, wherein the fluid sample is a filtered serum and the particulate substance includes at least one virus.

15. A method according to claim 11, wherein the step of detecting includes dispersing the emission light signal and detecting the dispersed emission light signal.

16. A method according to claim 15, wherein the step of analyzing includes effecting component analysis of the particulate substance in accordance with the detected dispersed emission light signal.

17. A method according to claim 15, wherein the irradiation light is provided with a wavelength outside of a wavelength range of a spectrum of the dispersed emission light signal.

18. A method according to claim 1, wherein the step of applying energy to the fluid sample includes applying an electric field having a strength above a breakdown threshold value of the particulate substance and below a breakdown threshold value of the fluid sample.

19. A method according to claim 18, wherein the step of detecting includes detecting an acoustic wave signal resulting from breakdown of the particulate substance.

20. A method according to claim 19, wherein the step of analyzing includes determining a number of the particulate substance by counting a number of the detected acoustic wave signals.

21. A method according to claim 19, wherein the step of analyzing includes measuring a particle size of the particulate substance in accordance with a pulse height of the detected acoustic wave signal.

22. A method according to claim 19, wherein the step of detecting further includes detecting an emission light signal resulting from breakdown of the particulate substance.

23. A method according to claim 18, wherein the step of detecting includes detecting an emission light signal resulting from breakdown of the particulate substance.

24. A method according to claim 23, wherein the step of detecting includes dispersing the emission light signal and detecting the dispersed emission light signal.

25. A method according to claim 24, wherein the step of analyzing includes effecting component analysis of the particulate substance in accordance with the detected dispersed emission light signal.

* * * * *